Figure 1:
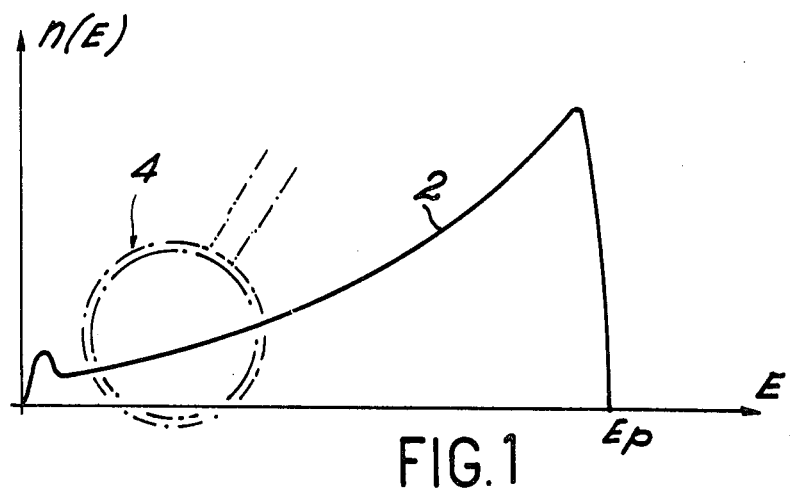

United States Patent [19]

le Gressus et al.

[11] 4,034,220
[45] July 5, 1977

[54] PROCESS AND APPARATUS FOR THE ELEMENTARY AND CHEMICAL ANALYSIS OF A SAMPLE BY SPECTRUM ANALYSIS OF THE ENERGY OF THE SECONDARY ELECTRONS

[75] Inventors: Claude le Gressus, Fontenay-le-Fleury; Daniel Massignon, Paris; René Sopizet, Chevilly-Larue, all of France

[73] Assignee: Commissariat a l'Energie Atomique, Paris, France

[22] Filed: Dec. 16, 1975

[21] Appl. No.: 641,240

[30] Foreign Application Priority Data

Jan. 2, 1975 France .............................. 75.00050
May 23, 1975 France .............................. 75.16206

[52] U.S. Cl. ................................ 250/310; 250/305; 250/307
[51] Int. Cl.² ...................................... G01N 23/225
[58] Field of Search .......... 250/305, 306, 307, 309, 250/310, 311

[56] References Cited

UNITED STATES PATENTS

| | | | |
|---|---|---|---|
| 3,461,306 | 8/1969 | Stout et al. | 250/306 |
| 3,535,516 | 10/1970 | Munakata | 250/310 |
| 3,678,384 | 7/1972 | Oatley | 250/310 X |

Primary Examiner—Eugene R. LaRoche
Attorney, Agent, or Firm—Flynn & Frishauf

[57] ABSTRACT

A process of elementary and chemical analysis of samples by spectrum analysis of secondary electrons emitted by the sample when it is subjected to a beam of monoenergetic primary electrons concentrated on its surface is characterized in that the intensity of a beam of monoenergetic primary electrons $E_p$ emitted by an electron gun is modulated according to a sinusoidal law at a frequency $\omega$, in that the secondary electrons of energy E emitted by the sample are collected, in that the intensity of the collected beam is detected by generating an electric detection signal proportional to the intensity, in that the intensity of the component of the frequency $\omega$ of the detection signal which provides the number of secondary electrons corresponding to the said energy is measured, and, in that the value of the collection energy E is modified in order to scan the energy spectrum comprised between the values $E_1$ and $E_2$ so that one obtains the spectrum n(E) of the intensity of the secondary electron emission of the sample as a function of the energy E.

17 Claims, 9 Drawing Figures

PROCESS AND APPARATUS FOR THE ELEMENTARY AND CHEMICAL ANALYSIS OF A SAMPLE BY SPECTRUM ANALYSIS OF THE ENERGY OF THE SECONDARY ELECTRONS

The present invention relates to a process of elementary and chemical analysis of a sample by spectrum analysis of the energy of secondary electrons emitted by the sample when this is exposed to a monoenergetic beam of primary electrons concentrated on the surface of the said sample.

The process according to the invention has particularly for its object the spectrum analysis of the energy of electrons emitted by Auger effect by the elements contained in the sample under analysis.

The process according to the invention as well as the apparatus for putting it into effect is concerned with the field of the electron microscope: one transmits a monoenergetic beam of electrons to a sample, a beam of electrons which sweeps the sample, the secondary electrons emitted by the sample under the effect of the primary beam being characteristic of the nature in the sample of atoms which are free or grouped in molecules or organised in structure (e.g. crystalline, amorphous.....).

It is known that the study of peripheral shells of electrons of the atoms, molecules or organised structures of the sample is carried out by the study of the spectrum of the secondary electrons (Auger, Coster-Kronig) emitted by the elements of the sample excited by the monoenergetic beam of primary electrons or emitted by the electrons diffused in the sample.

In order to explain these phenomena it is recalled that the Auger effect is an effect of internal conversion in an atom having been subjected to an ionisation. Thus when an electron of a monoenergetic primary beam of electrons strikes an atom of the sample with sufficient energy, an electron of the deep shell (shell K, for example) of the atom is ejected with energy $E_p - E_k$, $E_k$ being the energy of the electron in shell K and $E_p$ the energy of electrons of the primary beam. The electrons of the upper shells arriving to fill the spaces left in shell K freeing energy $E_k - E_l$, for example, if the replaced electron in shell K is an electron from shell L. This transition frees energy $E_k - E_l$ which is inthe form of the emission of a photon X or of the emission of an Auger electron coming from one of the upper shells of the nucleus, for example, an electron of shell M which is then emitted with energy $E_k - E_l - E_m$. The emission of electrons by the Auger effect thus permits the measuring of the electron occupation of the upper levels, particularly in the valency and conduction bands, of the atoms which are free or in organised structures. The rays emitted by each atom correspond to a transition from one characteristic shell of the element and allow the elementary and chemical analysis of the sample by studying the Auger spectrum analysis which is at once qualitative and quantative.

Generally, the Auger transitions are sought in the region between 0 and 10 KeV.

The invention applies particularly but not exclusively to the elementary and chemical examination of a sample by the spectrum of Auger emission from the body, emission of secondary electrons created by the impact of a beam of primary electrons having the same kinetic energy. The set of spectrums of electrons used to this end must conform with certain special characteristics for their performance to be of good quality. The area analysed on the sample must also be as small as possible. The sensitivity must be, for a give spatial revolution, sufficient to detect the presence of a body with weak concentration on a small area of the sample. As will hereafter become apparent, this sensitivity is partially related to the resolution in energy and to the sensitivity of the radiation detectors measuring the intensity of the secondary electrons emitted by the sample. It is further necessary to operate the primary beam at the weakest possible intensity in order that the high energy electrons of the primary beam do not degrade the sample, conditions absolutely necessary, for example, for the examination of biological products which are easily degraded; briefly, the operation must modify the state of the sample as little as possible. Further, in order to avoid all chemical change of the sample which is necessarily located in high vacuum, it is important that the examination of the sample should be as rapid as possible to avoid the chemical degradation phenomena such as, for example, the reduction of oxides of the sample. Finally, it is indispensable in order to separate the neighbouring Auger peaks, to analyse the spectral structure of these peaks and to detect the effect of chemical displacements, that the sensitivity of the spectroscopic energy examination must be of the order of a fraction of an electron volt.

The present invention has for a special object a process of elementary and chemical analysis of samples by spectrum analysis of secondary electrons emitted by the same sample when this is subjected to a beam of monoenergetic primary electrons concentrated on its surface, the process conforming with the spectral, geometric and temporal needs and characteristics previously set forth.

The process according to the invention is characterised in that the intensity of a beam of monoenergetic primary electrons $E_p$ emitted by an electron gun is modulated according to a sinusoidal law at a frequency $\omega$, in that the secondary electrons of energy E emitted by the sample are collected, in that the intensity of the said collected beam is detected by generating an electric detection signal proportional to the said intensity, in that the intensity of the component of the frequency $\omega$ of the said detection signal which provides the number of secondary electrons corresponding to the said energy is measured, and, in that the value of the collection energy E is modified in order to scan the energy spectrum comprised between the values $E_1$ and $E_2$ so that one obtains the spectrum n(E) of the intensity of the secondary electron emission of the sample as a function of the energy E.

In order to measure the component at the frequency $\omega$ of the said detection signal, one can operate either by filtering with the aid of a bandpass filter centered around the frequency $\omega$, or by synchronous detection in a phase sensitive demodulator by introducing into the said demodulator, on the one hand an electrical reference signal proportional to and in phase with the value of the sinusoidal modulation at the frequency $\omega$ of the beam of primary electrons and on the other hand the electric detection signal. One can equally proceed by correlation or numerical Fourier transformation of the detected signal in order to extract the component at the frequency $\omega$ after having put the signal in numerical form in a computer memory.

The process of the invention also permits the sweeping of the surface of the sample by the primary electron beam to achieve an elementary and chemical analysis of all the surface of the sample. Further, for each point of the sample, one can record the curve $n(E)$ of the electron intensity as a function of the energy of the emitted electrons. After numerical treatment in a computer one achieves a map of the sample showing the intensity of the peaks, Auger, for example, corresponding with a characteristic transition of an element. One thus obtains the geographic distribution of the concentration of various elements of the sample, an observation possible thanks to the rapidity of the analysis by the process according to the invention and by the increased sensitivity relative to the prior art.

The invention also relates to an apparatus including, in an evacuated chamber:

an electron gun comprising an electron emitting cathode and a device for the supply of a sinusoidal voltage at frequency $\omega$ to a Wehnelt electrode DC negatively biased with respect to the voltage of the said anode, a sample connected to earth, an electronic system for focussing on the sample primary electrons emitted by the electron gun, an analyser of the energy of secondary electrons emitted by the sample, a detector of the said analysed secondary electrons, delivering an electrical detection signal proportional to the number of secondary electrons detected, means connected with the said detector for measuring in the said detection signal the intensity of the component of the frequency $\omega$, and a recorder connected to the output of the said means.

The cathode of the apparatus according to the invention is, in a preferred embodiment of the invention, a heated filament which is maintained at a high negative potential; the sample serving to operate as the anode carrying relative to the cathode a high positive potential. According to the invention, the Whenelt electrode is polarised, that is to say, carries a continuous negative potential in relation to the emitting cathode. The electronic circuit comprising the emitting cathode, the Whenelt and the sample, is equivalent to the circuit of a triode operating in "Class A" in which the grid is biassed so as to allow to pass without distortion the modulation voltage applied to the Whenelt - grid. This feature is fundamental for, as will be seen later, it enables the modulation of the primary electron beam to be as sinusoidal as possible (that is to say, free of harmonics) with the object of achieving a demodulation without loss of information, which allows perceptible reductions of the mean intensity of the current of the primary electron beam. Also, the weak value of the current permits of no degradation of the sample particularly by heat and permits representative measurements as much of quality as of quantity.

Figure 2:
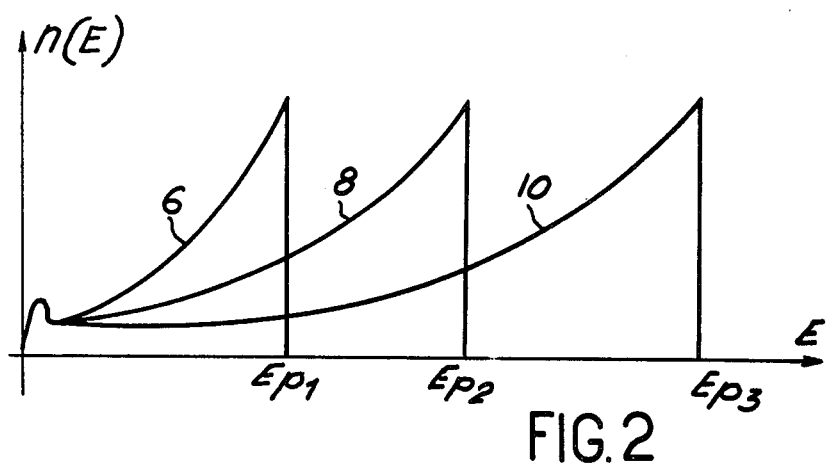
Figure 3:
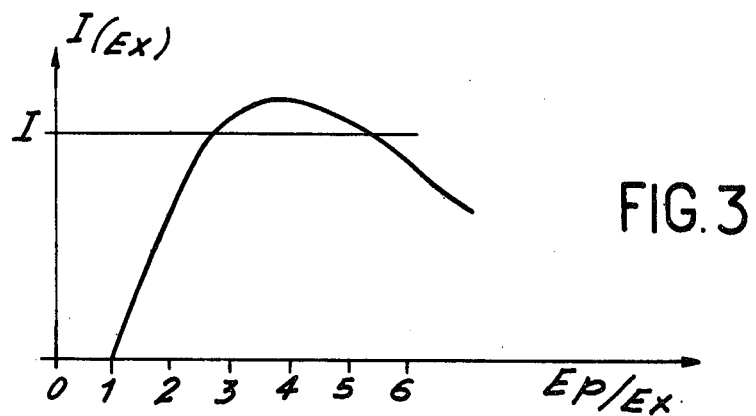
Figure 4:
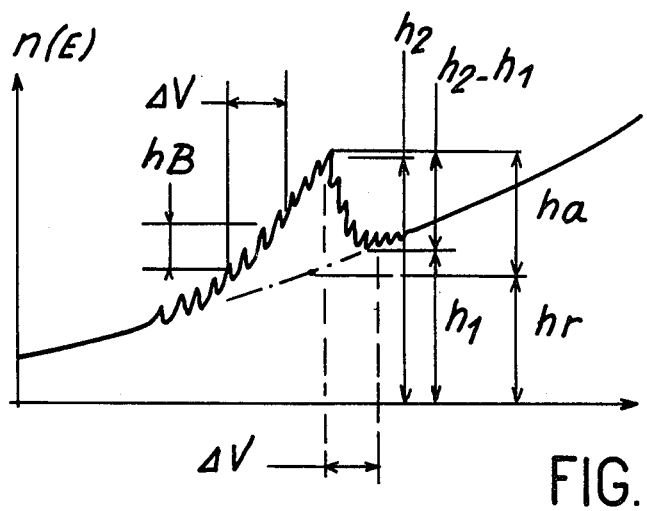
Figure 5:
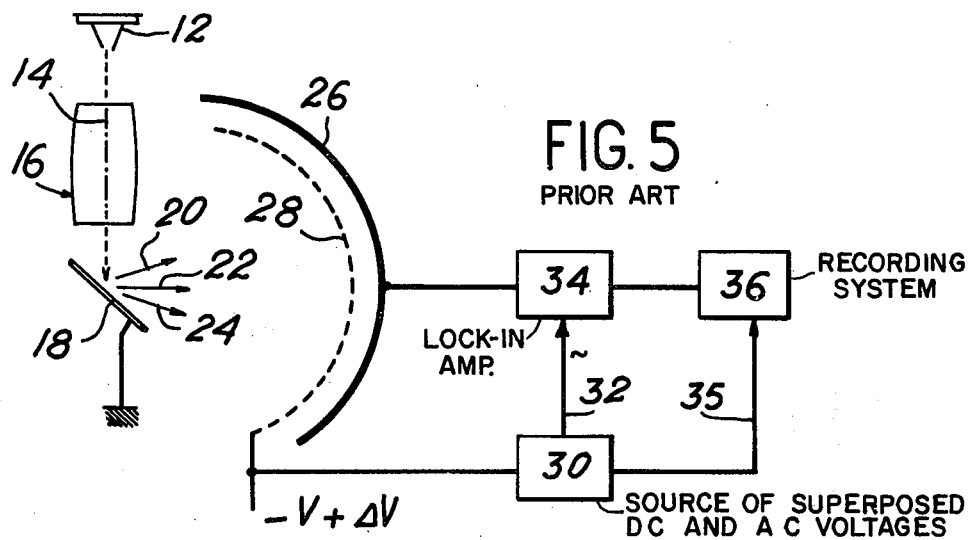
Figure 6:
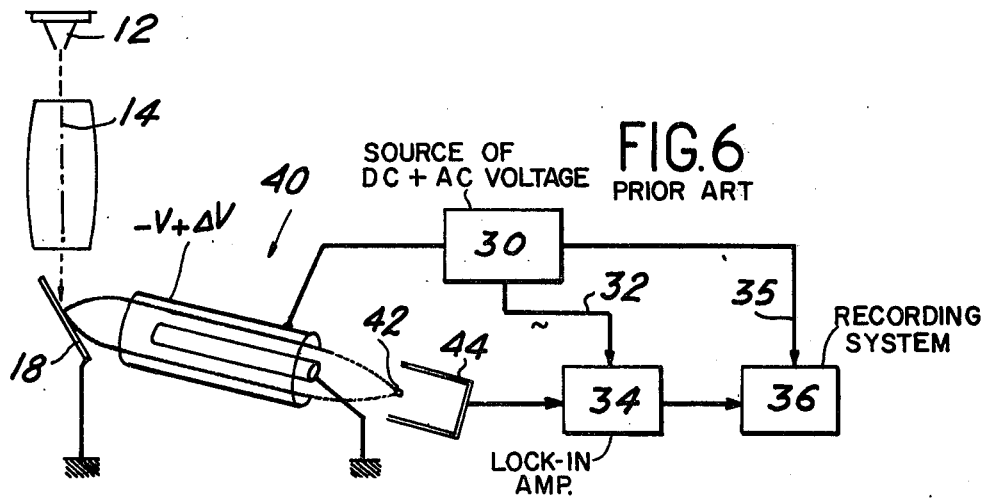
Figure 7:
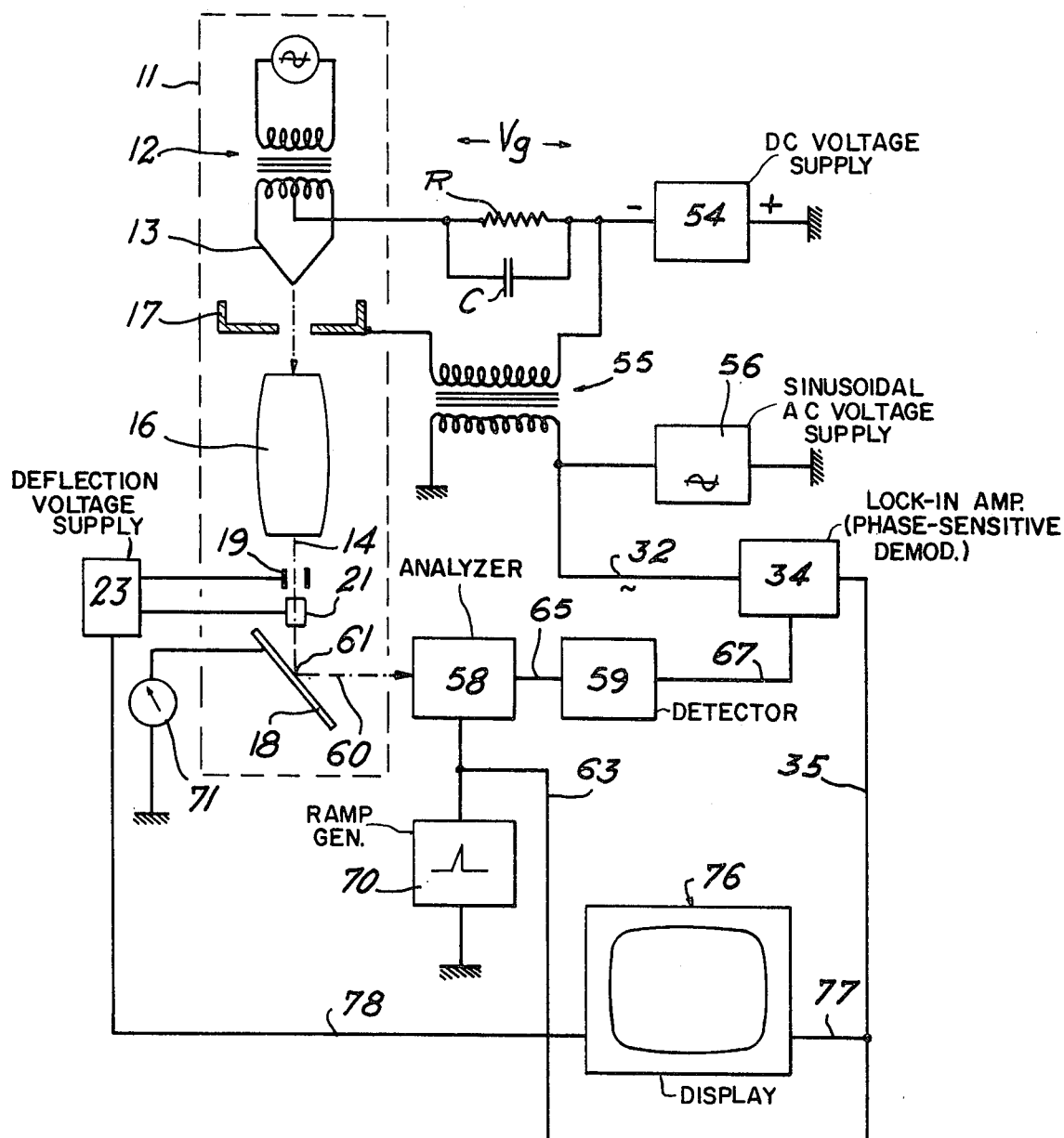
Figure 8:
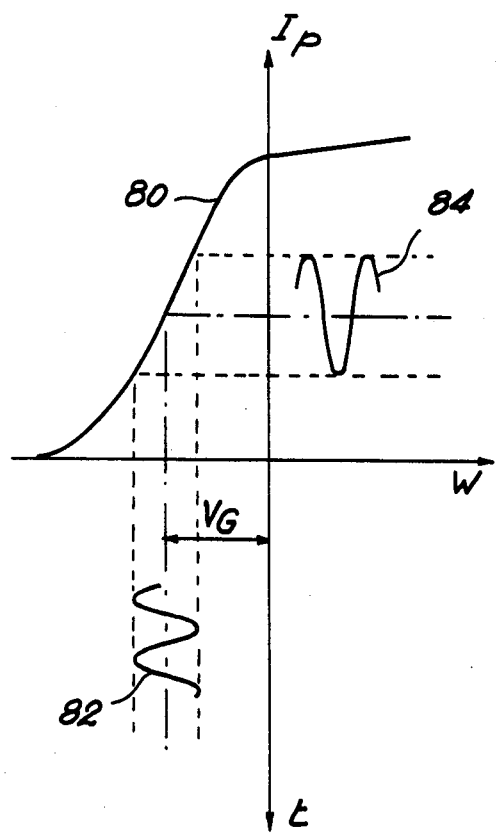
Figure 9:
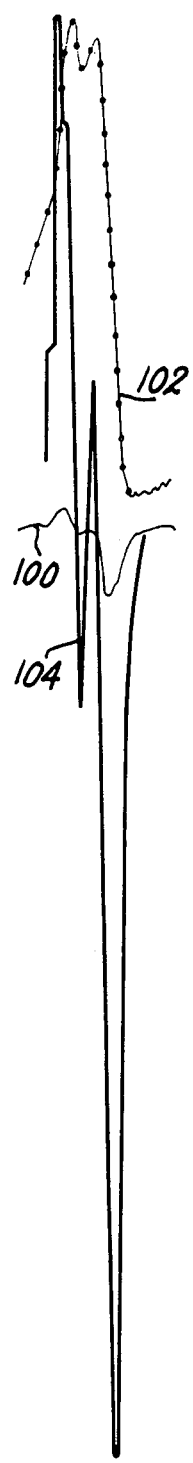

Other characteristics and advantages of the invention will appear better after the description which follows of embodiments given by way of example but not limitation with reference to the accompanying drawings in which are represented:

In FIG. 1, the curve of variation of the intensity of the secondary electrons as a function of the energy of the emission of the said primary electrons, In FIG. 2, the variation of the intensity of secondary electrons emitted by the different values of the energy $E_p$ of electrons of the primary electron beam, In FIG. 3, the variation of the intensity of the flow of Auger electrons emitted at energy $E_x$ as a function of the relationship $E_p/E_x$, In FIG. 4, a curve illustrating the different parameters of an Auger emission peak, In FIG. 5, an apparatus of known type for the spectrum analysis of secondary electrons emitted by the sample, the apparatus including a control grid, In FIG. 6, an apparatus for spectrum analysis by a cylindrical coaxial analyser, In FIG. 7, a block diagram of preferred apparatus according to the invention, In FIG. 8, an explanatory diagram of the amplification by modulation of the Whenelt electrode of the electron gun, and In FIG. 9, an Auger emission spectrum obtained according to the invention.

In FIG. 1, the curve $n(E)$ represents the density of secondary electrons emitted by a sample when the latter is bombarded by a beam of primary electrons of energy $E_p$. The energy of the emitted secondary electrons varies between O and $E_p$ and the curve 2 of FIG. 1 shows the general appearance of the curve $n(E)$. Given the low amplitude of the Auger peaks they are not seen on the curve of FIG. 1 but will be described with respect to FIG. 4 which represents the part of the curve 2 seen in the magnifying glass 4.

In FIG. 2, there is illustrated, by the curves 6, 8 and 10, the shape of the curves n(E) for the energy of flow of primary electrons $E_p$ at values $E_{p1}$, $E_{p2}$, $E_{p3}$.

In FIG. 3, there is illustrated the intensity $I(E_x)$ of emitted Auger electrons as a function of the ratio of the primary energy $E_p$ and the energy $E_x$. One sees that, in a certain region, the same value of the intensity I corresponds with two values of the ratio $E_p/E_x$.

In FIG. 4, there is shown the shape of an Auger peak with, as prescribed, the number of scattered electrons as a function of their energy. One can see from this curve that it is necessary to take into account three components of this signal:

The magnitude $h_r$ of back-scattering corresponds to the back-scattered electrons of energy $E_x$, The magnitude $h_b$ of the noise corresponding to random fluctuation of the signal, and, the magnitude $h_a$, the height of the Auger peak which represents the magnitude that one seeks to put in evidence.

The intensity of the emitted Auger electrons is about $10^{-4}$ times the primary intensity $I_p$. Combining the information of FIGS. 3 and 4 one can see that for a given energy $E_x$, one can practically, in a certain energy region, augment two or three times the primary energy without as much as significantly modifying the intensity of the Auger emission measured by the value $h_a$ but whilst modifying in important manner the magnitude $h_r$ of back-scattered electrons at energy $E_x$. As will later be seen, it is desirable to reduce as much as one can the intensity of the back-scattered electrons to avoid saturation of the amplifiers disposed at the ends of the intensity measuring system and other devices for detection of electrons of energy $E_x$ separated by the analyser.

There will now be described two prior art arrangements for detecting and analysing electrons emitted by the sample target. Two electrostatic analysers of actually existing energy will be described in schematic fashion: the system with a retarding grid such as is shown in FIG. 5, and the system of coaxial cylindrical analyser illustrated in FIG. 6.

In FIG. 5, there is shown an electron gun 12 sending a beam of primary electrons 14 through an accelerating and focussing lens 16. The beam of primary electrons of energy $E_p$ arrives on the sample target 18 electrically connected to earth, which causes the effect of a secondary electron emission illustrated by the arrows 20, 22 and 24. The emitted secondary electrons, particularly the Auger electrons, are collected by the grid 26. The spectrum analysis of the emitted electrons is afforded by a control grid 28 maintained at a continuous negative potential $-V$ to which is added an alternating potential $\Delta V = K\sin\omega t$. This control grid is fed by a supply 30 controlling at once the continuous voltage V and the sinusoidal variations $\Delta V$. The sinusoidal variations of the voltage imposed on the control grid 28 are sent by the line 32 to a phase sensitive amplifier 34 of which one input is connected to the collection grid 26. This phase detection amplifier or "lock-in" amplifier is followed by a recording system 36 detecting the number of electrons corresponding to an energy $E(E = _qV)$, an indication sent by the supply 30 in the cable 35 constituting one of the inputs to the recording system 36. The curve supplied by the recorder 36 is a curve which must be processed as will later be seen in order to give the form shown in FIG. 4.

In FIG. 6, there is represented another arrangement of the prior art consisting of a coaxial cylindrical analyser. The electrons emitted by the target sample 18 under the influence of the primary beam 14 are collected by the cylindrical coaxial analyser 40 which focusses the electrons at 42, electrons corresponding to the potential $-V$ applied to the cathode of the analyser supplied by the supply 30.

The cathode of the analyser is further maintained at a varying sinusoidal voltage $\Delta V = K\sin\omega t$. After collection in a channel electron multiplier 44, the voltages corresponding to the number of electrons of energy E are supplied to the phase sensitive amplifier 34 (as in the arrangement of FIG. 5) of which the output is connected to recorder 36.

In these two systems of the prior art, the analysis of the energy of the emitted electrons is made by the devices of the retarding control grid or the coaxial cylindrical analyser in which the grids or electrodes are modulated by a sinusoidal voltage $\Delta V = K\sin\omega t$. In the control apparatus of FIG. 5, the intensity I collected by the collecting grid 26 depends on the potential V applied to the retarding grid according to the formula:

$$I(V + \Delta V) = I(V + k\sin\omega t) =$$

$$I_o + \frac{\delta I}{\delta V} k\sin\omega t - \frac{1}{4} \frac{\delta^2 I}{\delta V^2} k^2\cos^2\omega t \ldots$$

If the reference voltage sent through the line 32 by the phase sensitive detector 34 is of frequency $\omega$ one effects a synchronous detection at frequency $\omega$ and the value of the output voltage of the phase sensitive amplifier 34 will be proportional to the magnitude $\delta I/\delta V$. In the system of the retarding control grid, the collected electrons on the grid are all those whose energy is greater than the value of the potential V. One has therefore $$I(V) = \int_{qV}^{Ep} n(E)dE$$

The derivative of the voltage I with respect to V, $\delta I/\delta V$ of the above formula is therefore proportional to the curve $n(E)$. The synchronous detection at frequency $\omega$ thus gives in the system of the retarding grid the curve $n(E)$ of FIG. 4. A detection at frequency $2\omega$ determines the variation of the derivative with respect to the energy of the curve $n(E)$ as a function of the energy. In the case of the coaxial analyser of FIG. 6, the system being focussing, only the electrons comprised in the modulation window $\Delta V$ (illustrated in FIG. 4) reach the detector 44. A synchronous detection at frequency $\omega$ thus shows the variation of the derived curve $$\frac{dn(E)}{dE} = f(E)$$

As shown by the development in a Taylor series, the signal collected in 44 is proportional to the amplitude of modulation, so much so that the odd terms can be neglected, that is to say, for the weak values of modulation. As one has seen from FIG. 4, the presence of noise $h_b$ which is not negligible with respect to the amplitude $h_a$ of the Auger peak necessitates a phase detection system for eliminating the noise of random frequency. In the prior art systems, schematically shown in FIGS. 5 and 6, the sinusoidal variation of voltage (permitting the scanning of energy and the detection by phase sensitive amplifiers) was made in the analyser of the energy of emitted electrons.

This entails numerous disadvantages: the uncertainity of the energy, that is to say, the experimental width of the spot 42 of the electron separated by the coaxial analyser is proportional to the modulation amplitude $\Delta V$. The weaker values of modulation usable in practice comprise between one and two volts which is very bad with respect to the intrinsic resolution of the coaxial analyser (for example, of the order of 0.2 volt around an energy of 100 volts). This means that the resolution of the energy of the apparatus does not exceed the value of $2e$ V imposed by the variation of the retarding potential (grid system) or focussing (cylinder system); the peaks of which the separation in energy is less than $2e$volts will not be separated by the analyser. On the contrary, as will later be seen, the apparatus according to the invention permits the use of all the sensitivity of the analyser.

With respect to FIG. 4, it is seen that a sinusoidal variation of $\Delta V$ corresponds with an Auger peak at two magnitudes $h_1$, $h_2$ and an amplitude variation $h_2$-$h_1$. In the phase detection system there corresponds to the values $h_1$ and $h_2$ a relatively weak variation of phase $\Delta\phi$ proportional to the variation $h_2$-$h_1$. This form of detection is only efficient when the curve $n(E)$ experiences rapid variations of slope. The noise $h_B$ compared to $h_a$ not being negligible, it is necessary to make the lock-in of phase sensitive amplifier function with long time constants of integration approaching a second and with medium sensitivity (three hundred $\mu V$), this in order to eliminate the changes due to the significant noise with respect to the phase changes corresponding to an energy variation $\Delta V$. Thus, the only way of reconciling:

the elimination of noise in the recorded spectrum (choice of the time constant equal to three hundred milliseconds or even one second), the analysis in good conditions of energy resolution (amplitude of modulation below or equal to 2 volts), the finding of impurities of weak concentrations, which corresponds to weak intensity of the Auger peak, imply the use of guns of high electron supply (intensity of current 1 to 50 microamps, for example) and slow speeds of analysis (energy scanning); the spectrum corresponding to the total curve $n(E)$ is obtained in 500 seconds, for example, with a coaxial analyser.

In spite of the use of the electronic lens, the use of electron beams of high intensity limits the spatial resolution of the classical type of Auger microscopes (one micron resolution for one microampere of strength) and introduces an important degradation of samples; thermal reduction of oxides or diffusion of impurities in the analysed volume, for example.

One can say that the conditions obtained in the prior art with the help of the apparatus mentioned for the analysis of elements are:

Analyser: amplitude of modulation—V = 2 volts
Gun: $Ip = 10^{-7}$ amperes
Spatial resolution: 5000 A in diameter
Phase sensitive amplifier: Time constant: 300 milliseconds, sensitivity 100 microvolts; time of recording of the spectrum 500 seconds, from which a detection threshold of 1% atomic is obtained with a coaxial analyser.

In FIG. 7, there is shown an apparatus according to the invention for producing an Auger spectrum of the sample. An electron gun 12 comprises a heated filament (cathode) 13 which sends a beam of primary electrons 14 onto a sample target 18 connected to earth by the intermediary of a weak current measuring device 71. The assembly is placed in an evacuated enclosure 11. A concentrating lens of the beam is diagrammatically shown at 16 and the beam electrons 14 are accelerated between the emitting cathode 13 and the sample 18, the said sample comprising the anode. It is the voltage continuously delivered by the supply 54 between cathode 13 and anode sample 18 which determines the energy $E_p$ of electrons of the primary beam 14. In turn the intensity of the beam is determined by the biassing of the Wehnelt electrode 17 playing the part of modulation grid. The voltage maintained between the emitting cathode and the Wehnelt electrode 17 is the voltage $V_g$ developed between the ends of the adjustable resistor R. The capacitor C is a decoupling capacitor. According to the invention, the voltage of the Wehnelt electrode is sinusoidally modulated by the transformer 55 supplied by the sinusoidal voltage generator 56. The secondary electrons 60 emitted at the focussing point 61 by the sample 18 are analysed in an analyser 58. The output of this analyser 58 is joined by the connection 65 to a detector (channel electron multiplier, for example) delivering a signal sent by the line 67 to a phase sensitive demodulator 34.

The input to the phase sensitive demodulator of known type by the line 32 is a reference voltage provided from the generator 56 of sinusoidal voltage for the Wehnelt electrode; the output of the phase sensitive demodulator is a signal which is sent to the recorder 36. The signal giving the values of energy E of secondary electrons selected are further sent by the line 63 to the recorder 36 to give the values of the abscissa.

The scanning of energy is achieved by the device 70 providing a voltage ramp corresponding to the interval $E_1$-$E_2$ applied to the analyser 58. In a preferred form of the invention the analyser 58 is a cylindrical coaxial analyser but alternatively one can use a grid analyser. These analysers are shown in FIGS. 5 and 6.

The invention consists essentially in eliminating the modulation of the voltage applied to the control electrode of the analyser 58 and in achieving an electron gun with a purely sinusoidal modulation of brilliance according to the drawing of FIG. 7 in which the intensity of the primary electron beam is modulated.

It has been found that the sample current such as can be measured by the ammeter 71 between the sample and earth does not offer appreciable distortion with respect to the sinusoidal biassing of the Wehnelt electrode.

The emitted Auger intensity being proportional to the intensity of the primary electron current, it is modulated according to the same sinusoidal law and the Auger intensity will be proportional to the amplitude of the sinusoidal modulation of brilliance of the electron gun. It is the same for the intensity of back-scattering. Referring to FIG. 4, one will choose a primary energy scale $E_p$ determined by the biassing of the sample anode 18 supplied by the continuous supply 54 in a manner such that the sum $h_r + h_a$ (FIG. 4) will be compatible with the dynamic scale of the phase sensitive demodulators or amplifiers and with the ratio $h_a/h_4$ being as great as possible. The modulation of the intensity of the beam of electrons emitted by the gun or brilliance modulation returns therefore to impose a degree of modulation able to reach 100% of the total sum $h_r + h_a$ and no longeras in the prior art a variation $h_2$-$h_1$ (FIG. 4) weak with respect to the noise in the voltage modulation interval of the analyser of the prior art. Further, the variation of phase in the apparatus using a phase sensitive demodulator is, for a large part, due to the variation of the Auger intensity $h_a$, which permits study of a very weak variation particularly in the neighbourhood of the extremes of the curve $n(E)$. In the course of an amplitude of modulation of 100%, the vector sum $h = h_r + h_a$ varies between zero and $h$ maximum whilst the mean noise remains constant. One sees then that the change of phase becomes very important and that consequently in the detection mode the signal/noise ratio is very high which offers substantial advantages: one can reduce by 100 times the primary current without loss of information, one can further work on sensitivities of $30\mu V$ of energy on the analyser without being inconvenienced by a high noise level.

To measure the components of frequency $\omega$ of the output signal of the detector 59 one can equally well utilise a bandpass filter (not shown) centred around the frequency $\omega$ and located between the detector 59 and the recording device 36. In this case, the device 34 for the detection of the component of frequency $\omega$ is not connected by the line 32 to the generator 56. One can alternatively use a real time correlator for measuring the component of frequency $\omega$, a correlator already known to the man skilled in the art, or even a device for effecting a Fourier transformation. All means for extracting the signal component at a frequency $\omega$ are included in the scope of the invention and represented in FIG. 7 by the device 34.

In a preferred embodiment of the invention, one uses a coaxial cylinder as the analyser 58 permitting a more rapid time response. As, thanks to the apparatus of the invention employing modulation of the intensity of the beam 14, there is less sensitivity to noise in the measuring sequence, one can also work with time constants of integration in the phase sensitive amplifier which are much more rapid, of the order of some tens of milliseconds only, thus reducing considerably the analysis time which can be from 10 to 50 seconds for an energy scan displayed at around 1000 volts. To avoid the duration of analysis being limited by the time constant of the X-Y recorder 36 one can use an oscilloscope or else an analogue to digital converter sending the different signals corresponding to a given energy E to a computer memory.

Reduction of the intensity of the primary beam entails a better focussing and the spatial resolution becomes less than a thousand A.

To improve the sensitivity one can arrange after the coaxial analyser a scintillator provided with a photomultiplier before the phase sensitive detector or any other device receiving the component of the detected signal of frequency $\omega$.

In the table which follows is summarised an embodiment and the parameters concerned:

Tungsten filament gun,
Degree of modulation 60% on the Wehnelt electrode,
Frequency of modulation 3KHz,
$I_p = 10^{-9}$ ampere,
Spatial resolution: better than one thousand A,
Energy resolution the same as the intrinsic resolution of the analyser (0.2eV for an energy of 100eV),
Time of recording of the spectrum 50 seconds,
Time constant of the phase sensitive detector: 30 milliseconds,
Sensitivity of the lock-in demodulator 30 $\mu$V giving a detection threshold of the order of 0.1%.

In another embodiment:
Tungsten filament gun,
Degree of modulation 100%,
Frequency of modulation 1.5 KHz,
$I_p = 5 \times 10^{-8}$ A,
Spatial resolution: better than 1000 A,
Energy resolution, time of recording and time constant as in the preceding example,
Signal/Noise ratio better than 100 for the Auger peak 93 of silicon which gives a detection threshold better than 0.01% atomic.

To increase the spatial resolution one uses in a variant embodiment of the invention a gun with a crystal of Lanthanum Hexaborate (LaB$_6$) giving a spatial resolution better than 500 A, all other parameters being the same as before. If one wishes still further to improve the spatial resolution to bring it to around 100 A, one uses in another variant embodiment a field emission gun. The significance of the apparatus according to the invention for observing biological systems is then very clear. A supplementary advantage of the invention connected with the use of a coaxial cylindrical analyser is that by the modulation of the intensity of the primary beam associated with a phase detection of frequency $\omega$ connected with the frequency $\omega$ of modulation of the intensity of the primary beam, there is detected, no longer the derivative $dn$ (E)/$dE$ of the curve of the intensity of emitted secondary electrons as a function of the energy as in the prior art but the curve $n$(E) itself which opens the way to quantitative analysis whilst avoiding the renormalisations imposed by the necessary integrations when one only obtains the derivatives $dn$ (E)/$dE$.

It goes without saying that the type of recording is that which enables one to store in a computer data corresponding to a scanning of a spectrum $n$(E). Further, one can use magnetic analysers of known type.

In FIG. 8 there is shown the biassing and amplification diagram for modulation of the Whenelt electrode of the electron gun. The assembly of the emitting cathode, Whenelt - grid and anode sample constitutes a form of triode. It goes without saying that it will be possible within the scope of the invention to dissociate the role of the anode from the sample and interpose a supplementary anode plate. In the drawing of FIG. 8 there is shown in the abscissa the value of the intensity of the primary current $I_p$ as a function of the voltage W between the emitting cathode and the Whenelt electrode. This type of diagram is well known to electronics engineers. One regulates the value of the resistance R of FIG. 7 in order that the biassing voltage of the Whenelt grid $V_G$ corresponds sensibly to the modulation point of the curve 80, $I_p = f(W)$ which is the transfer characteristic of the electron gun 12 of FIG. 7. One sees that the sinusoidal modulation of the voltage between the Whenelt electrode and the cathode as a function of time represented by the curve 82 translate as sinusoidal modulation of the intensity of the current $I_p$ without significant distortion (curve 84). This point is very important, since, the modulation of brilliance or of the intensity being purely sinusoidal, the measure of the intensity of the component of the beam of secondary electrons at the frequency $\omega$ reduces to a demodulation in a very narrow frequency spectrum without loss of information. This phenomenon entails the possibility of using very weak primary currents $I_p$, notably currents between $10^{-7}$ and $10^{-10}$ A with signal to noise ratios greater than 10.

In FIG. 9 there is shown a spectrum obtained according to the invention compared with a spectrum obtained by the prior art. On the curve 102 there is shown the variation $n$(E) of the intensity of the beam of secondary electrons as a function of the energy, the curve of variation obtains thanks to the system according to the invention. On the curve 104 is shown the value of the derivative $dn$ (E)/$dE$ of this curve obtained numerically. On the curve 100 there is shown the curve $dn$ (E)/$dE$ obtained with a coaxial energy modulated analyser apparatus of the prior art for an amplitude of modulation of 2 volts. The process and the apparatus employed according to the invention permits the obtaining of a spectrum 104 which is purer and more detailed than the curve 100, while illustrates the progress made.

A final advantage of the invention is that it permits the scanning of a spectrum rapidly and the avoidance of the degradation of the sample chemically or physically. In order to effect an analysis of the sample over all the surface, one scans, with the help of the deflection plates 19 and 21 (FIG. 7) supplied from the supply 23, the beam 14 on the surface of the sample 18. In the prior art in order to obtain a signal as strong as possible, one uses a strong modulation of the cathode of the coaxial analyser which as already seen has a detrimental effect on the energy resolution. A modulation of the order of 20eV was usual which did not permit the making of an image of the distribution of chromium by its Auger peak of 523 eV and a distribution of oxygen by its peak of 510 to 513 eV. In the circumstances of the prior art the scanning of the surface lasted 100 seconds which corresponds to a dwell time per point of 25 microseconds (there are $4.10^{-6}$ image points in one image). In these conditions the modulation frequency was 30KHz, the time constant of the lock-in of 10mS, the maximum sensitivity employed 10$\mu$V. The "AUGER" image could really only be obtained for those elements in greater concentrations in the sample.

The process according to the invention (sinusoidal modulation of the brilliance of the primary electron beam) considerably enhancing the signal to noise ratio permits:

A reduction of the primary electron current,
Leads to an improved spatial resolution,
Renders possible the distribution image of trace elements,
Can be obtained in the case of fragile degradable samples in a shorter time.

The improvement offered by giving the curve $n(E)$ directly permits use of a calculator (recorder) 36 of which the interface is simple to achieve but which offers a considerable advantage in the successive registration of spectra of distribution images.

The response time of the analyser (coaxial cylinder type) being very rapid, for dwell times of the spot 61 on each point of $100\mu S$ at the maximum, one can for each image point record the curve $n(E)$ in its entirety. Each recorded point is treated successively by a smoothing function of known type, and there is reconstructed on an electronic display the exact variations of $n(E)$ in each selected energy channel: for example, Si-92eV. For a single scan of the surface one then possesses the whole information, one can consider that each point has been represented in its real physico-chemical state and all information collected corresponds to the same state. This point is essential with regard to the destruction of samples: even when a spectrum is recorded in 50 seconds between the recording of the Auger transition of Si at 92eV at time $t=1$ seconds and the recording of the Auger transition of oxygen for example at 510 eV at time $t = 50$ seconds, a bombardment of the surface is produced which lasts 50 seconds during which the surface is changed (non-stoichiometric oxides being formed for example). If one no longer wishes to limit the Auger spectrometry to the study of bare surfaces and of absolutely pure samples, it is necessary at all costs to neutralise these rapid changes under electronic bombardment:

By reducing the primary current (sinusoidal brilliance modulation).

Diminishing the time of acquisition of the data.

The time of acquisition is a fundamental point; the time of processing and of reconstruction (smoothing of each curve, derivation) is less important and can be done on a small peripheral calculator. The classical apparatus for processing the information has only been represented by the visual display device 76 without too much detail because the device is well known. The display 76 has supplied thereto by way of the line 77 information corresponding to the height of the Auger peak and by the line 78 the location of the spot 61 determined by the potential applied to the plates 19 and 21. There is thus made a map of the Auger emission of the surface of the sample at given energy E, or for an energy interval between $E_1$ and $E_2$.

What we claim is:

1. Process of elementary and chemical analysis of a sample by analysing energy spectra of secondary electrons emitted by the said sample when it is subjected to a beam of monoenergetic primary electrons concentrated on its surface, characterised in that:

the intensity of the beam of monoenergetic primary electrons emitted by an electron gun is modulated in accordance with a sinusoidal law at a frequency $\omega$, the beam of secondary electrons having an energy E is collected, the intensity of the said collected beam is detected by generating an electrical detection signal proportional to the said intensity, in the said detection signal there is measured the intensity of the component at the frequency $\omega$ which gives the number of secondary electrons, corresponding to the said energy, the value of the energy of collection E is changed in order to scan an energy spectrum comprised between two limits $E_1$ $E_2$, which is done so that the spectrum $n(E)$ is obtained of the intensity of the secondary electron emission from the sample as a function of the energy E.

2. Process according to claim 1, characterised in that in order to measure the intensity of the component of the detection signal at the frequency $\omega$, there is supplied to a phase sensitive detector an electric reference signal proportional and in phase with the value of the sinusoidal modulation at the frequency $\omega$ of the primary electron beam, and the said electrical detection signal.

3. Process according to claim 1, characterised in that for measuring the intensity of the component at the frequency $\omega$ of the detection signal, the said signal is filtered around the said frequency $\omega$.

4. Process according to claim 1, characterized in that the step of measuring, in the detection signal, the intensity of the component of the frequency $\omega$ is performed by correlation on a signal previously recorded in a memory element of a computer.

5. Process according to claim 1, characterized in that the spectrum $n(E)$ representing the emission spectrum of secondary electrons from the sample for a point on the sample is recorded, then the surface of the sample is scanned by the primary electron beam for recording the said curve $n(E)$ at each point of a raster of points on the surface of the sample.

6. Apparatus for analysis of a sample by energy spectra of secondary electrons, characterized in that there is included in an evacuated chamber:

an electron gun comprising an electron emitting cathode, and a device for supplying a sinusoidal voltage at the frequency $\omega$ to a Wehnelt electrode biased at a negative voltage continuously with respect to the said cathode and thereby modulating the electron beam emitted by said electron gun, a sample connected to earth, an electronic system for focussing on the sample primary electrons emitted by the electron gun, an analyser of the energy of the second electrons emitted by the sample responsive to secondary electrons having a particular level of energy and having means for varying said energy level over a range of energy level, a detector of the said secondary analysed electrons delivering an electric detection signal proportional to the number of secondary detected electrons having said particular energy level, means connected to the said detector for measuring in the said signal the intensity of the component at the frequency $\omega$, a recorder connected to the output of said means.

7. Apparatus according to claim 6, characterised in that the analyser is a retarding grid analyser.

8. Apparatus according to claim 6 characterised in that the analyser is a coaxial cylinder analyser.

9. Apparatus according to claim 8 characterised in that the coaxial cylinder analyser is followed by a channel multiplier.

10. Apparatus according to claim 8 characterised in that the coaxial cylinder analyser is followed by a scintillator and a photomultiplier.

11. Apparatus according to claim 6, characterised in that the said means for measuring the intensity of the component at the frequency $\omega$ of the said detection signal are constituted by a phase sensitive de-modulator connected at the output of the said detector and to the sinusoidal supply device of the Wehnelt electrode.

12. Apparatus according to claim 6, characterised in that the said means for measuring the intensity of the component of the frequency $\omega$ of the said signal of detection are constituted by a bandpass filter centred on the frequency $\omega$.

13. Apparatus according to claim 6, characterised in that the said means for measuring the intensity of the component at the frequency $\omega$ of the said detection signal are constituted by a real time correlator.

14. Apparatus according to claim 6 characterised in that the electron gun is a thermo-electronic gun having a tungsten cathode.

15. Apparatus according to claim 6 characterised in that the electron gun is an electronic gun having a cathode of $LaB_6$.

16. Apparatus according to claim 6, characterised in that the electron gun is a field emission gun.

17. Apparatus according to claim 6 characterised in that it further includes deflection electrode means for scanning the point of impact of the beam of primary electrons on the sample.

* * * * *